United States Patent
Hamaker et al.

(10) Patent No.: US 11,504,392 B2
(45) Date of Patent: Nov. 22, 2022

(54) HYDROGEL

(71) Applicant: Purdue Research Foundation, West Lafayette, IN (US)

(72) Inventors: Bruce R Hamaker, West Lafayette, IN (US); Xiaowei Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 49 days.

(21) Appl. No.: 17/020,889

(22) Filed: Sep. 15, 2020

(65) Prior Publication Data

US 2021/0085708 A1 Mar. 25, 2021

Related U.S. Application Data (60) Provisional application No. 62/902,442, filed on Sep. 19, 2019.

(51) Int. Cl.
| | |
|---|---|
| *A61K 31/717* | (2006.01) |
| *A61K 9/06* | (2006.01) |
| *A61K 9/00* | (2006.01) |
| *A23L 29/212* | (2016.01) |
| *A23L 2/68* | (2006.01) |
| *C08L 1/02* | (2006.01) |

(52) U.S. Cl.
CPC ............. *A61K 31/717* (2013.01); *A23L 2/68* (2013.01); *A23L 29/212* (2016.08); *A61K 9/0095* (2013.01); *A61K 9/06* (2013.01); *C08L 1/02* (2013.01); *A23V 2002/00* (2013.01)

(58) Field of Classification Search
CPC ............................ A61K 31/717; A23L 29/212
See application file for complete search history.

(56) References Cited

U.S. PATENT DOCUMENTS

| | | |
|---|---|---|
| 5,766,662 A | 6/1998 | Inglett |
| 6,482,430 B1 | 11/2002 | Weightman et al. |

OTHER PUBLICATIONS

Wang et al. ("Rheological properties and structural characteristics of arabioxylan hydrogels prepared from three wheat bran sources", Journal of Cereal Science (Jul. 1, 2019), Published by: Academic Press, vol. 88, pp. 79-86. (Year: 2019).*
Zhang X. et al., Acid gelation of soluble laccase-crosslinked corn bran arabinoxylan and possible gel formation mechanism. Food Hydrocolloids 92 (2019) 1-9.
Berlanga-Reyes C. et al., Enzymatic Cross-Linking of Alkali Extracted Arabinoxylans: Gel Rheological and Structural Characteristics. Int. J. Mol. Sci. 2011, 12, 5853-5861.
Mendez-Encinas M., et al., Ferulated Arabinoxylans and Their Gels: Functional Properties and Potential Applicatior as Antioxidant and Anticancer Agent. Oxidative Medicine and Cellular Longevity, 2018, 1-22.

* cited by examiner

*Primary Examiner* — Leigh C Maier
*Assistant Examiner* — Everett White
(74) *Attorney, Agent, or Firm* — Purdue Research Foundation (57) ABSTRACT

The present disclosure relates to a novel hydrogel, and to method of making and using the novel hydrogel. The novel hydrogel is a reaction product of a water soluble laccase cross-linked arabinoxylan and an acid, and has a pH value of 1.5-2.5.

12 Claims, 7 Drawing Sheets

HYDROGEL

TECHNICAL FIELD

The present disclosure relates to a novel hydrogel, and method of making and using the novel hydrogel. The novel hydrogel is a reaction product of a water soluble laccase cross-linked arabinoxylan and an acid, and has a pH value of 1.5-2.5.

BACKGROUND

This section introduces aspects that may help facilitate a better understanding of the disclosure. Accordingly, these statements are to be read in this light and are not to be understood as admissions about what is or is not prior art.

Hydrogels are three dimensional hydrophilic or amphiphilic polymer networks that are capable of retaining large amounts of water or biological fluids. Polymer interactions that lead to the formation of hydrogels include hydrogen and ionic bonding, hydrophobic interactions, and covalent crosslinks. For example, high-methoxyl pectin forms a gel when sufficient sugar and acid are present to reduce hydration and negative charge, and promote hydrophobic interactions. In gelling of sodium alginate, addition of calcium ions create ionic bridges with acid groups to form an irreversible gel. Chitosan-polyvinyl alcohol form gels in the presence of glutaraldehyde as the covalent crosslinking agent.

Food polysaccharides are non-toxic, biocompatible, biodegradable, either water-soluble or extractable in food-grade solvents, and generally have high swelling ability. These are properties that make them well suited for food uses, as well as for biomedical, pharmaceutical, and cosmetic applications. Arabinoxylan is a type of plant polysaccharide found in cell walls of endosperm and bran tissues of cereals and other monocot seeds. They are either soluble in water or extractable in dilute alkali. Arabinoxylans consist of a linear backbone chain of β-D-xylopyranosyl residues linked through (1,4) glycosidic bonds with various compositions of branched structures. α-L-Arabinofuranosyl residues are attached to some or most of the Xylp residues at O-2, O-3, and/or O-2,3 positions. Arabinoxylans can be neutral or acidic depending whether they contain 4-O-methyl-D-glucuronopyranosyl or D-glucuronopyranosyl substituents. Ferulic acid is commonly esterified on the O-5 position of arabinose branches. It was reported that there are about 75 ferulic acid residues esterified to one corn bran arabinoxylan (CAX) polymer that has a degree of polymerization of about 2000, with many of the residues participating in diferulate crosslinks that makes CAX largely insoluble in the cell wall matrix. De-esterification using alkali (e.g., sodium hydroxide) to remove crosslinks brings these polymers into solution, and residual bound ferulic acid plays an important role in the functionality of CAX. CAX solutions can form gels through oxidative crosslinking of bound ferulic acid moieties, and gel strength is associated with the ferulic acid content of arabinoxylan. A strong gel was formed by the crosslinking action of laccase in CAX extracted with mild alkali that removes diferulate crosslinks, but retains much of the uncrosslinked bound ferulic acid. When treated with high concentration of alkali, no arabinoxylan gel formed due to low ferulic acid content; and bound ferulic acid content was associated with the structural properties of the gel, including pore size and crosslinking density.

Although there are certain reported hydrogel materials, there are still need for low pH low sugar gels as food polysaccharides in food product s, as well as in other food gels and as a drug delivery matrix.

SUMMARY

The present disclosure relates to a novel hydrogel, and to method of making and using the novel hydrogel.

In one embodiment, the present disclosure provides a hydrogel, wherein the hydrogel has a pH value of 1.5-2.5, wherein the hydrogel is a reaction product of a water soluble laccase cross-linked arabinoxylan and an acid.

In one embodiment, the present disclosure provides a method of using the novel hydrogel, wherein the hydrogel is ingested in a beverage to form a gel in low pH environment of the stomach to delay gastric emptying and increase satiety.

DETAILED DESCRIPTION

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

Figure 1:
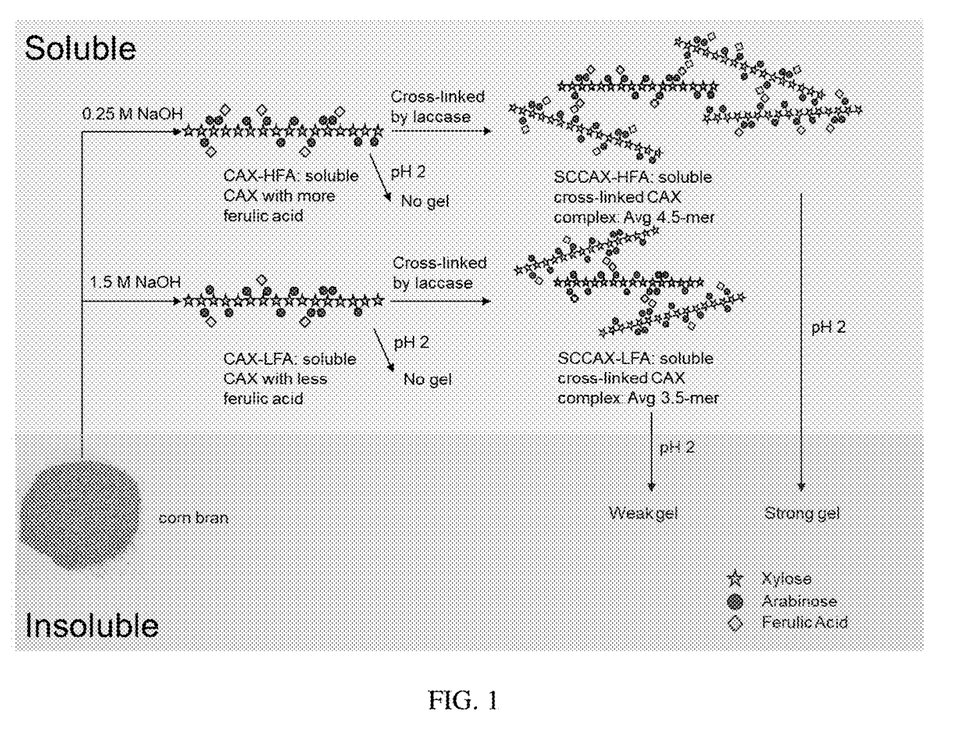
FIG. 1: Illustration of novel gel formation of corn arabinoxylan. Alkali-extracted CAX was treated with laccase to form soluble crosslinked CAX (SCCAX) complex, which then formed gels when pH was reduced to 2.

The present disclosure provides a novel type of gel formation, where a soluble laccase-crosslinked CAX (SC-CAX) complex forms a gel simply by lowering pH. Differently, high-methoxyl pectin requires high sugar content to gel at low pH, however low acyl gellan gum similarly demonstrates acid gelation though is different in its solubility characteristics (requires either a chelating agent or heat to solubilize). The overall scheme of formation of the low pH SCCAX gel is shown in FIG. 1.

Potential applications of this kind of low pH gelling polysaccharide are low sugar low pH gels or a beverage containing SCCAX that might be taken with gelling occurring in the low pH environment of the stomach for the purpose of providing a satiating effect and lowering glycemic response due to slow gastric emptying. Moreover, arabinoxylan is an important cereal fiber that possesses health-promoting effects in the gut due to colonic fermentation. This new gel type based on CAX treatment could also have broader applications as food gels and drug delivery matrices In one embodiment, the present disclosure provides a hydrogel, wherein the hydrogel has a pH value of 1.5-2.5, wherein the hydrogel is a reaction product of a water soluble laccase cross-linked arabinoxylan and an acid.

In one embodiment regarding the hydrogel of the present disclosure, wherein the acid used for the reaction product is a water soluble inorganic acid. In one aspect, the acid is hydrochloric acid.

In one embodiment regarding the hydrogel of the present disclosure, wherein the hydrogel has a pH value of 1.8-2.2. In one aspect, the hydrogel has a pH value of about 2.0.

In one embodiment regarding the hydrogel of the present disclosure, wherein the hydrogel is a pH reversible gel.

In one embodiment regarding the hydrogel of the present disclosure, wherein the hydrogel is a thermally reversible gel.

In one embodiment regarding the hydrogel of the present disclosure, wherein the hydrogel is a pH reversible and a thermally reversible gel.

In one embodiment regarding the hydrogel of the present disclosure, wherein the arabinoxylan used for laccase crosslinking is obtained from an alkali treated corn bran. In one aspect, the arabinoxylan used for laccase crosslinking had an arabinose/xylose ratio between 0.15 to 0.3. In one aspect, the alkali is KOH or NaOH.

In one embodiment regarding the hydrogel of the present disclosure, wherein the laccase cross-linked arabinoxylan has a 2-10 wt % of the total weight of the hydrogel.

In one embodiment, the present disclosure provides a method of using a hydrogel of any embodiment of the present disclosure, wherein the hydrogel is added to a food or beverage product as a low sugar and low pH additive.

In one embodiment, the present disclosure provides a method of using a hydrogel of any embodiment of the present disclosure, wherein the water soluble laccase cross-linked arabinoxylan as a hydrogel is ingested in a beverage to form a gel in low pH environment of the stomach to delay gastric emptying and increase satiety.

MATERIALS AND METHODS

Materials. Corn bran was obtained from Agricor (Marion, Ind., USA). Thermostable α-amylase, proteinase, laccase from *Trametes versicolor*, ferulic acid, 3,4,5-trimethoxycinnamic acid (TMCA), methanolic-HCl, and sodium hydroxide were obtained from Sigma-Aldrich (St. Louis, Mo., USA). Hexane, ethanol, and concentrated hydrochloric acid were bought from Mallinckrodt Chemicals (Phillipsburg, N.J., USA). Tri-Sil and acetonitrile was obtained from Fisher Scientific (Thermo Fisher Scientific, Suwanee, Ga., USA). Ultrapure water was prepared by a Millipore Ultra-Genetic polishing system with $<5 \times 10^{-9}$ TOC and resistivity of 18.2 mΩ (Millipore, Billerica, Mass., USA) and used for all experiments.

Arabinoxylan extraction from corn bran. Corn bran was defatted by suspending in hexane (solid to liquid ratio 1:10) and stirring for 30-45 min. The slurry was filtered and repeated once. The final residue was dried in a hot air oven at 45° C. The defatted bran was then suspended in water and pH was adjusted to 7.0 using sodium hydroxide. The slurry was boiled with constant stirring for 5 min to gelatinize the starch. Thermostable α-amylase (4 mL per 100 g bran) was added after cooling the suspension to 90° C. and kept for 60 min to hydrolyze starch. The pH was adjusted to 6 with HCl after cooling the solution. Proteinase (5 mL per 100 g bran) was added and incubated for 4 h at 50° C. The enzyme was inactivated by boiling the mixture for 5 min. The slurry was centrifuged at 10,000 g for 20 min and washed with purified water twice. The final pellet was dried in a hot air oven at 45° C. to obtain de-starched bran (DSB). DSB (50 g) was suspended in 500 mL of sodium hydroxide solution (0.25 M and 1.5 M). After stirring for 24 h at room temperature, the suspension was centrifuged at 10,000 g for 10 min. The supernatant pH was adjusted to 4-5 using concentrated hydrochloric acid. The arabinoxylan was precipitated from the supernatant with 4 volumes of absolute ethanol. The precipitate was dried in a hot air oven at 45° C., re-dissolved in water and freeze-dried. Thus, two samples CAX-low ferulic acid (LFA) and CAX-high ferulic acid (HFA), extracted from 1.5 M and 0.25 M sodium hydroxide, respectively, were obtained.

Arabinoxylan crosslinking and gel formation. Arabinoxylan preparations (2%, w/v) were dissolved in purified water by stirring at room temperature. Then, laccase (1.675 nkat/mg arabinoxylan) was added. The reaction was kept for 24 h at room temperature and laccase was deactivated by boiling the samples for 10 min. Residual laccase activity was measured by using 0.0216 mM syringaldazine in methanol as substrate (Figueroa-Espinoza & Rouau, 1998), and no laccase activity was found. After crosslinking, samples were freeze-dried. Two samples, soluble crosslinked CAX (SC-CAX)-LFA and SCCAX-HFA, the product of laccase treatment of CAX-LFA and CAX-HFA, respectively, were obtained. Samples were stored in a vacuum desiccator until further use.

Arabinoxylan gels were prepared by dissolving SCCAX-LFA and SCCAX-HFA in hydrochloric acid solution (pH 2). SCCAX-LFA (3% and 5%, w/v) and SCCAX-HFA (3% and 5%, w/v) were mixed at 150 rpm in an Eppendorf Thermo-Mixer C (Eppendorf, Hauppauge, N.Y., USA) at 37° C. until samples were dissolved. Preliminary experiments showed that SCCAX-HFA and SCCAX-LFA did not form gel mixed at pH 3, 4, and 5, while gel formed immediately when pH was reduced to 2.

Ferulic acid and diferulic acid content of arabinoxylan. The determination of ferulic acid and diferulic acid (DFA) content of arabinoxylan followed a protocol previously described with minor modification. Briefly, 5 mL of 2 M NaOH was added to 50 mg of CAX-LFA, CAX-HFA, SCCAX-LFA and SCCAX-HFA. The mixtures were allowed to react for 18 h under nitrogen, were protected from light, and continuously stirred. After adding 25 μg of 3,4,5-trimethoxy-cinnamic acid (TMCA) as an internal standard, 0.95 mL of concentrated HCl was added to adjust pH to 2. Phenolics were extracted three times with 4 mL of diethyl ether, and dried under nitrogen. The dried extracts were re-dissolved in 1 mL of methanol, filtered through a 0.22 μm nylon membrane (Agilent Technologies, Santa Clara, Calif., USA) for HPLC (Agilent 1100, Agilent Technologies, Santa Clara, Calif., USA) analysis.

HPLC was performed using an Agilent Eclipse XDB-C18 column (250×9.4 mm, i.d. 5 μm; Agilent Technologies, Santa Clara, Calif., USA) monitored at 320 nm. Temperature of the column oven was set at 35° C. The elution gradient (mobile phase A: acetonitrile; mobile phase B: sodium acetate buffer 0.05 M, pH 4.0) used was: 15-35% A in 30 min, 35-60% A in 0.5 min, 60-15% A in 4.5 min, and 15% A for 5 min. Flow rate was 1 mL/min and the injection volume was 20 μL.

Structural features of arabinoxylan. Protein content of arabinoxylan was measured by the Micro BCA™ Protein Assay Kit according to manufacturer's instructions (Thermo Fisher Scientific, Waltham, Mass., USA). The molecular weight and size of arabinoxylan was analyzed by an Agilent 1100 high pressure size exclusion chromatography (HPSEC) equipped with refractive index (RI) and multiangle light scattering (MALS) detector (Agilent Technologies, Santa Clara, Calif., USA). Superdex 200 and 30 columns (GE Healthcare Bio-Sciences, Pittsburgh, Pa., USA) was used to separate the polymers. The HPSEC conditions were: mobile phase was purified water, injection volume was 100 μL, flow rate was 0.4 mL/min. Neutral and acidic monosaccharide composition of the arabinoxylan samples was determined as their trimethylsilyl (TMS) derivatives. An Agilent 7890A gas chromatograph and 5975C insert MSD with a triple-axis detector (Agilent Technologies, Santa Clara, Calif., USA) was used. Helium was the carrier gas at a flow rate of 1 mL/min through an Agilent DB-5 capillary column. Injection volume was 0.2 μL at a split ratio of 50/1. Oven temperature was initially 140° C., held for 2 min, and increased by 2° C./min to 180° C., held for 1 min, and increased at 30° C./min to 235° C. where it was held for 15 min.

Solution shear rheology. Solutions (3% w/v) of arabinoxylans were prepared in hydrochloric acid solution (pH 5 and pH 2). Storage and loss moduli under small amplitude oscillatory shear and viscosity was measured using a TA ARES-G2 rotational rheometer (TA Instruments, Newcastle, Del., USA) with a 40 mm 1.999° cone plate and using a 55 μm gap at 37° C. Flow curves were obtained over a shear rate range from 0.1 to 100 s$^{-1}$. Viscoelastic properties of the gels were measured by a frequency sweep test in a range of frequencies from 0.06 to 15.78 rad/s and a 3% strain, which was determined to be within the linear viscoelastic region.

Measurements were performed in triplicate and rheological parameters were calculated using the manufacturer's supplied computer software (TRIOS v4.0, TA Instruments, Newcastle, Del., USA). The viscosity of arabinoxylan solution samples was described by the power law model given by the equation below:

$$\eta = K\dot{\gamma}^{n-1}$$

Where η is apparent viscosity (Pa s), K is the consistency coefficient (Pa s$^n$), $\dot{\gamma}$ is the shear rate (s$^{-1}$) and n is flow behavior index.

Small amplitude oscillatory shear rheometry, temperature sweep test. The effect of temperature on gel storage was studied by loading the gel onto a TA ARES-G2 rotational rheometer (TA Instruments, Newcastle, Del., USA) with a 40 mm 1.999° cone plate. The storage and loss modulus were measured from 25 to 95° C. and temperature step was set at 5° C. A 3% strain and a 1 Hz frequency were applied. Measurements were performed in triplicate and rheological parameters were calculated using the manufacturer's supplied computer software (TRIOS v4.0, TA Instruments, Newcastle, Del., USA).

Cryogenic scanning electron microscopy (Cryo-SEM) of gels. SCCAX gels (3% w/v) were prepared by dissolving SCCAX-LFA and SCCAX-HFA in hydrochloric acid solution (pH 2). After gelling, gels were put into slit holders in the cryo-holder, secured in place with a set screw, and plunged into a liquid nitrogen slush. A vacuum was pulled and the samples were transferred to a Gatan Alto 2500 pre-chamber (cooled to −170° C.). After fracturing the samples with a cooled scalpel to produce a free-break surface, samples were sublimated at −90° C. for 10 min followed by sputter coating for 120 s with platinum. Then, the samples were transferred to the microscope cryo-stage (−120° C.) for imaging. The samples were imaged with a FEI NOVA nanoSEM field emission SEM (FEI Company, Hillsboro, Oreg., USA) using the ET (Everhart-Thornley) detector operating at 5 kV accelerating voltage, ~4.5 mm working distance, spot 3, and 30 μm aperture. Magnifications were 1,000×-5,000× for images.

Surface charge of arabinoxylan. CAX-LFA, CAX-HFA, SCCAX-LFA and SCCAX-HFA (3%, w/v) were dispersed in purified water and mixed until dissolved with an Eppendorf ThermoMixer C (Eppendorf, Hauppauge, N.Y., USA) at 37° C. The ζ-potential of the samples were measured using a Zetasizer Nano ZS90 (Malvern Instruments, Malvern, UK). All measurements were carried out at 25° C. and performed in triplicate.

FT-IR spectra of arabinoxylan at different pH's. Solutions (3%, w/v) of SCCAX-HFA and SCCAX-LFA were prepared in pH 2 and pH 5 hydrochloric acid solution and then analyzed using Fourier-transform infrared (FT-IR) spectroscopy. Spectra were obtained with a Nexus 670 FT-IR spectrometer (ThermoNicolet, Madison, Wis., USA) equipped with a deuterated triglycine sulfate (DTGS) detector and diamond attenuated total reflectance (ATR) crystal. Data were analyzed using OMNIC software (ThermoElectron Corp., Madison, Wis., USA).

Statistical analysis. Data were reported as mean±SD for triplicate determinations. One-way ANOVA and Tukey's test were employed to identify differences in means. Statistics were analyzed using SPSS for Windows (version rel. 10.0.5, 1999, SPSS Inc., Chicago, Ill., USA) and Origin for Windows (version Srl b9.3.1.273, OriginLab Corp., Northampton, Mass., USA).

Results and Discussion

Arabinoxylan gels have been made by others using laccase treatment to crosslink the ferulic acid residues of the soluble polysaccharide, however they form at about pH 5 and subsequent to the addition of laccase. The mechanism of this gel formation is the covalent diferulate crosslink, which forms a polymer network that traps water. Here, a different kind of arabinoxylan gel was formed. The illustration in FIG. 1 shows that laccase treatment of CAX mediated the formation of a soluble crosslinked corn arabinoxylan (SC-CAX) intermediate, which formed a gel on pH reduction. It is believed that the soluble intermediate formed with laccase, rather than a gel, because the arabinoxylan used had a low arabinose/xylose ratio with coinciding lower feruloylated arabinose branches. This appears to be a new polysaccharide-based gel type, in which the soluble arabinoxylan in water alone forms a gel at low pH. It is differentiated from the low pH gel-forming property of high-methoxyl pectin that requires high sugar content to restrict water availability to the pectin, though is similar in gelling properties to low acyl gellan gum. However, gellan gum is different from SCCAX in that it is not readily soluble in water requiring either heat or addition of a chelator. From a practical standpoint, SCCAX gels could be used in applications where low sugar low pH gels are desired or where a beverage containing SCCAX might be taken with gelling occurring in the low pH environment of the stomach.

Two soluble arabinoxylan samples were produced with alkali treatments, CAX-high ferulic acid (CAX-HFA) and CAX-low ferulic acid (CAX-LFA, FIG. 1). Laccase-treated CAX-HFA and CAX-LFA formed SCCAX-HFA and SCCAX-LFA, respectively, which were soluble crosslinked CAX complexes of limited polymerization. Weak and strong gels were formed by lowering pH of solutions of SCCAX-LFA and SCCAX-HFA, while no gels were formed at low pH for uncrosslinked CAX-HFA and CAX-LFA. Gel structure dissipated when pH was increased to 5, showing it to be a pH-reversible gel type. Structural features, rheological properties, and parameters related to a possible formation mechanism are shown below.

Monosaccharide, ferulic acid and diferulic acid content of arabinoxylan samples. As shown in Table 1, CAX was composed of arabinose (~15%), xylose (~68%), glucose (~5%), galactose (~5%), and glucuronic acid (~1.5%). CAX had a low arabinose/xylose ratio of about 22% compared to a typical CAX value of ~50% (Table 1). Low concentration of sodium hydroxide to extract CAX led to high residual ferulic acid; and high concentration of alkali resulted in greater ferulic acid depletion. It was reported that ferulic acid contents ranging from 2.1 to 15.0 mg/g when extracted with 0.5-1.5 M sodium hydroxide for 24 h, which was significantly higher than that of the present study of 0.61 and 1.15 mg/g (Table 2). The lower content of ferulic acid was associated with less arabinose branching in the CAX starting material and is likely the reason that no direct gels were formed by laccase treatment. Corn genotype and environment causes variation in ferulic acid contents, and likely explains the low content of ferulic acid in this study.

TABLE 1

Neutral and acidic monosaccharides composition and protein content of arabinoxylan[a]

| Samples | Arabinose (%) | Xylose (%) | Galactose (%) | Glucose (%) | Glucuronic acid (%) | Protein (mg/g) |
|---|---|---|---|---|---|---|
| CAX-LFA | 15.21a ± 3.07 | 68.11a ± 1.03 | 5.99a ± 1.03 | 5.65a ± 0.43 | 1.44a ± 0.06 | 57.78c ± 2.57 |
| SCCAX-LFA | 15.41a ± 1.13 | 67.46a ± 0.56 | 4.84a ± 0.56 | 4.92a ± 0.50 | 1.53a ± 0.16 | 113.38a ± 2.57 |
| CAX-HFA | 16.76a ± 1.71 | 67.58a ± 0.50 | 5.60a ± 0.49 | 5.86a ± 0.81 | 1.56a ± 0.54 | 22.89d ± 4.11 |
| SCCAX-HFA | 16.11a ± 0.68 | 68.89a ± 0.89 | 4.78a ± 0.48 | 5.09a ± 0.48 | 1.56a ± 0.16 | 75.04b ± 1.80 |

[a]CAX-LFA and CAX-HFA stand for corn bran arabinoxylan extracted by 1.5M and 0.25M NaOH, respectively; SCCAX-LFA and SCCAX-HFA stand for crosslinked CAX-LFA and CAX-HFA, respectively.

TABLE 2

Ferulic acid and diferulic acid (DFA) content in CAX and SCCAX[b].

| Samples | Ferulic acid (mg/g) | 8,8-DFA (mg/g) | 5,5-DFA (mg/g) | 8,5(benzofuran)-DFA (mg/g) | 8,5(decarboxylated)-DFA (mg/g) | Total DFA (mg/g) |
|---|---|---|---|---|---|---|
| CAX-LFA | 0.61b ± 0.06 | 0.47a ± 0.08 | 0.18ab ± 0.01 | 0.38b ± 0.07 | nd | 1.04b ± 0.05 |
| CAX-HFA | 1.15a ± 0.06 | 0.69a ± 0.10 | 0.36a ± 0.05 | 1.05a ± 0.15 | nd | 2.09a ± 0.20 |
| SCCAX-LFA | 0.10c ± 0.02 | 0.49a ± 0.09 | 0.02c ± 0.00 | nd | 0.51a ± 0.11 | 1.02b ± 0.31 |
| SCCAX-HFA | 0.30c ± 0.09 | 0.65a ± 0.14 | 0.04b ± 0.00 | nd | 0.66a ± 0.14 | 1.34ab ± 0.01 |

[b]CAX-LFA and CAX-HFA stand for corn bran arabinoxylan extracted by 1.5M and 0.25M NaOH, respectively; SCCAX-LFA and SCCAX-HFA stand for crosslinked CAX-LFA and CAX-HFA, respectively. nd stands for not detected. Data are expressed as mean ± SD (n = 3). Sample values marked by the different letters are significant different ($P < 0.05$).

After laccase treatment, remaining uncrosslinked ferulic acid decreased (Table 2). In CAX-HFA, 0.85 mg/g ferulic acid formed crosslinks in SCCAX-HFA, and a lesser 0.51 mg/g of ferulic acid of CAX-LFA was involved in crosslinking of SCCAX-LFA. Diferulic acids (DFA), including 8,8-DFA and 5,5-DFA, were found in both CAX and SCCAX. No significant change of 8,8-DFA was observed after laccase treatment while 5,5-DFA content of SCCAX was markedly lower than CAX. 8,5(benzofuran)-DFA was only found in CAX, while 8,5(decarboxylated)-DFA was only found in SCCAX (Table 2). Taken together, the DFA contents were not increased after laccase treatment, but rather it stayed at the same level. This phenomenon was previously reported and explained to be due to undetected DFA species.

Figure 2:
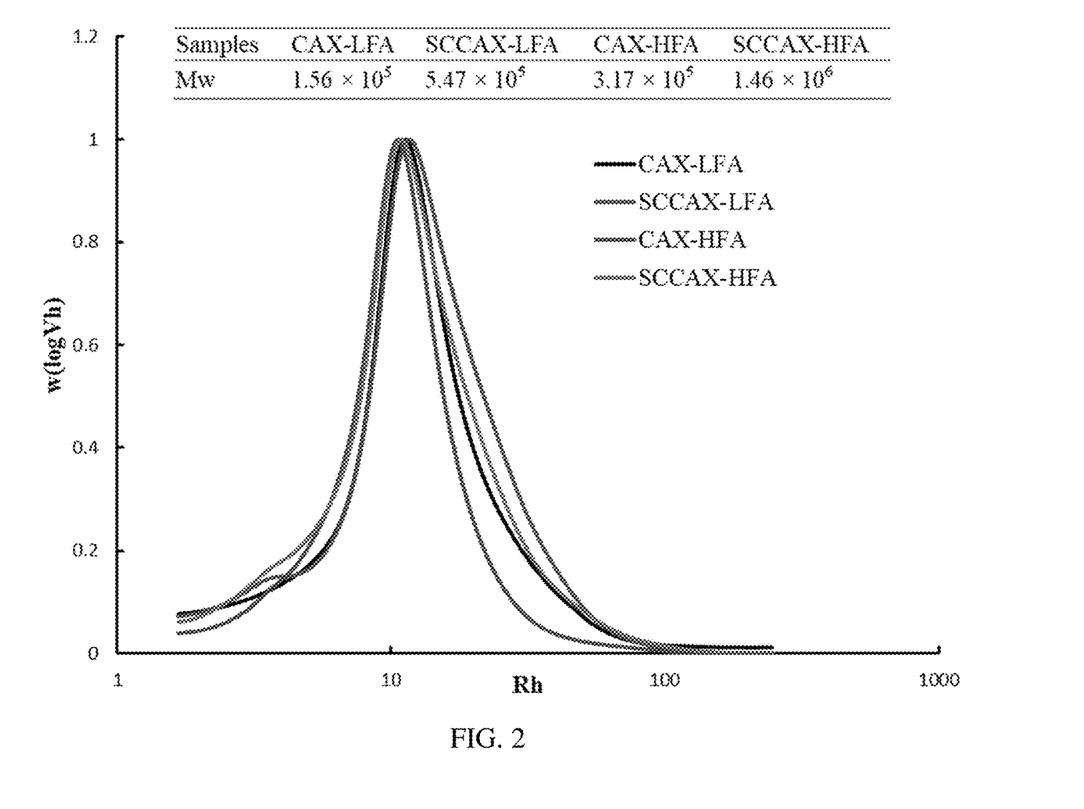
FIG. 2: Size exclusion chromatography of arabinoxylan samples. CAX-LFA and CAX-HFA are corn bran arabinoxylans extracted in 1.5 M and 0.25 M NaOH, respectively; SCCAX-LFA and SCCAX-HFA are soluble crosslinked CAX-LFA and CAX-HFA, respectively.

Molecular size of arabinoxylan samples. To examine whether SCCAX complexes formed after laccase treatment, HPSEC was used to determine the molecular size of arabinoxylan samples. As shown in FIG. 2, SCCAX-HFA had the largest hydrodynamic radius (Rh), followed by CAX-HFA, SCCAX-LFA, and CAX-LFA. CAX-HFA showed larger Rh than CAX-LFA as higher alkali treatment removed more ferulic acid residues, resulting in fewer crosslinks formed during laccase treatment of arabinoxylan polymers. Also, SCCAX-HFA and SCCAX-LFA had larger Rh than CAX-HFA and CAX-LFA, respectively. Thus, instead of gel formation, laccase treatment of CAX induced the crosslinking of arabinoxylan and produced SCCAX complexes, which was in agreement with the ferulic acid content change of between CAX and SCCAX (Table 2). The Mw of arabinoxylan from the MALS detector showed that CAX-LFA and CAX-HFA formed average 3.5-mer and 4.5-mer SCCAX complexes after laccase treatment, respectively (FIG. 2).

Figure 3:
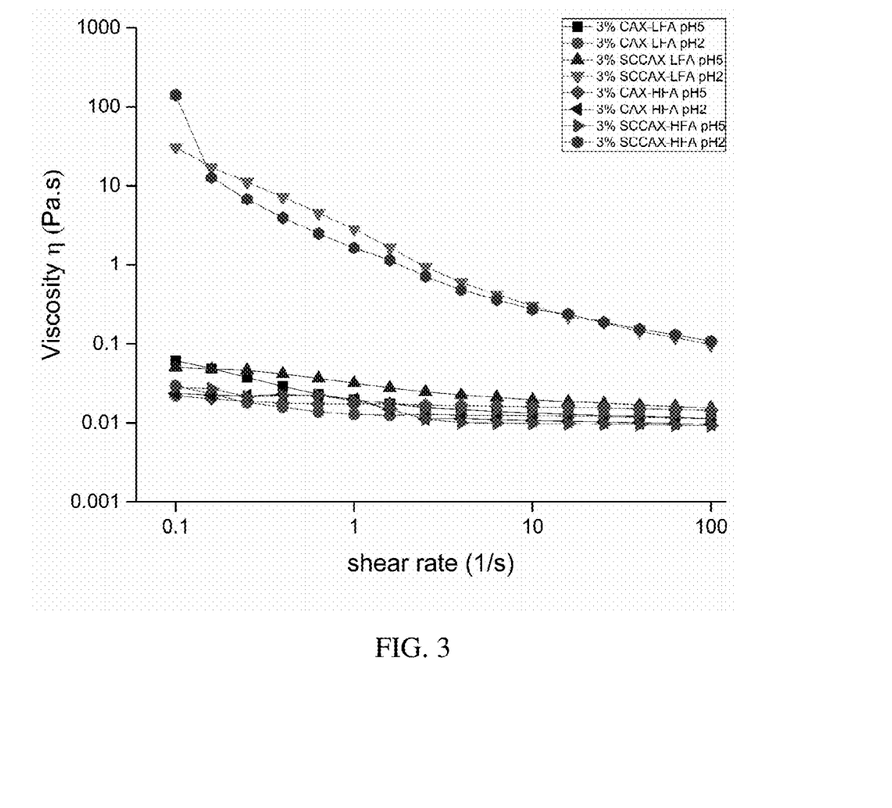
FIG. 3: Shear rate dependence of viscosity for arabinoxylans at a concentration of 3 wt %. CAX-LFA and CAX-HFA are corn bran arabinoxylans extracted in 1.5 M and 0.25 M NaOH, respectively. SCCAX-LFA and SCCAX-HFA are soluble crosslinked CAX-LFA and CAX-HFA, respectively.

Rheological characterization of arabinoxylans at different pHs. Shear viscosity versus shear rate profiles of 3% solutions of CAX-LFA, CAX-HFA, SCCAX-LFA and SCCAX-HFA at different pH values are shown in FIG. 3. All samples at pH 5, and CAX-LFA and CAX-HFA at pH 2, showed shear thinning behavior at low shear rates followed by Newtonian behavior at higher shear rate. Shear-thinning behavior was observed in SCCAX-HFA and SCCAX-LFA at pH 2. Both SCCAX-HFA and SCCAX-LFA at pH 2 revealed significantly higher solution viscosity than at pH 5, indicating that decrease the pH of SCCAX samples increased viscosity. This property was only found for the SCCAX samples, while no significant viscosity change was observed in the uncrosslinked CAX samples (FIG. 3). Overall, all samples showed a pseudo-plastic behavior, which was confirmed by the flow behavior indices (n<1) as shown in Table 2.

Within the linear region, flow curves of arabinoxylan were fitted to the Power-Law model in order to describe the apparent viscosity as a function of shear rate (Table 3). All data fitted well within the model, as $R^2$ values remained above 0.997. Higher flow consistency indices (K) were shown by SCCAX-LFA and SCCAX-HFA at pH 2. In addition, lower flow behavior index (n), and therefore higher pseudo-plastic behaviors were displayed by SCCAX-LFA and SCCAX-HFA. Thus, pH decrease of SCCAX complex increased the viscosity of the solution and the behavior of the solution changed to shear-thinning from Newtonian behavior. Moreover, all samples at pH 5, and CAX-LFA and CAX-HFA at pH 2, showed low viscosity (lower K) and displayed Newtonian behavior (n near 1, Table 3).

TABLE 3

Power law model parameters of arabinoxylan at the concentration of 3% (w/v)[c]

| Samples | Model parameters | | |
|---|---|---|---|
| | K(Pa s$^n$) | n | $R^2$ |
| CAX-LFA, pH 5 | 0.016 | 0.922 | 0.999 |
| CAX-LFA, pH 2 | 0.014 | 0.945 | 0.999 |
| SCCAX-LFA, pH 5 | 0.024 | 0.900 | 0.999 |
| SCCAX-LFA, pH 2 | 0.773 | 0.548 | 0.997 |
| CAX-HFA, pH 5 | 0.012 | 0.948 | 0.999 |
| CAX-HFA, pH 2 | 0.012 | 0.949 | 0.999 |
| SCCAX-HFA, pH 5 | 0.017 | 0.954 | 0.999 |
| SCCAX-HFA, pH 2 | 0.701 | 0.593 | 0.999 |

[c]CAX-LFA and CAX-HFA stand for corn bran arabinoxylan extracted by 1.5M and 0.25M NaOH, respectively; SCCAX-LFA and SCCAX-HFA stand for crosslinked CAX-LFA and CAX-HFA, respectively.

Figure 4:
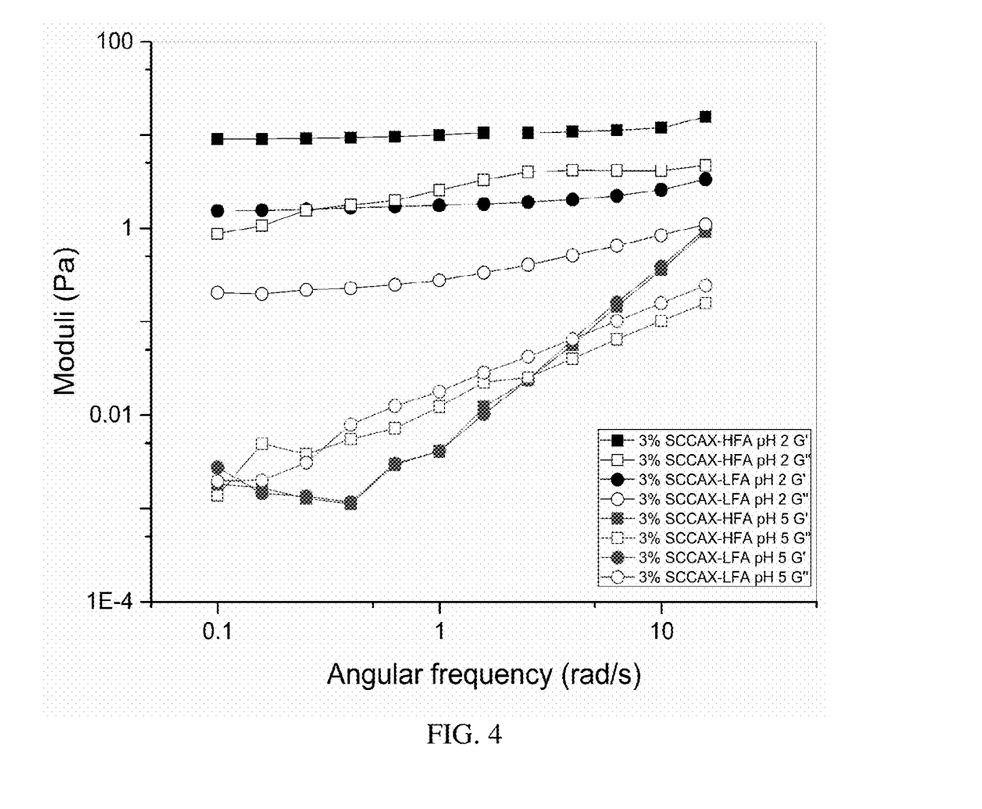
FIG. 4: Mechanical spectra of SCCAX-HFA and SCCAX-LFA at pH 2 and 5 at a concentration of 3 wt %. CAX-LFA and CAX-HFA are corn bran arabinoxylans extracted in 1.5 M and 0.25 M NaOH, respectively. SCCAX-LFA and SCCAX-HFA are soluble crosslinked CAX-LFA and CAX-HFA, respectively.

Viscoelasticity measurements were performed to determine the gelation property of SCCAX-HFA and SCCAX-LFA at pH 2 and 5. As shown in FIG. 4, at pH 5, no gel was formed for SCCAX-HFA and SCCAX-LFA and they exhibited the characteristic of a solution. When the pH was decreased to 2, G' of both SCCAX-HFA and SCCAX-LFA was greater than G", and G' was independent of frequency, indicating that a strong gel was formed.

Figures 5, 5B:
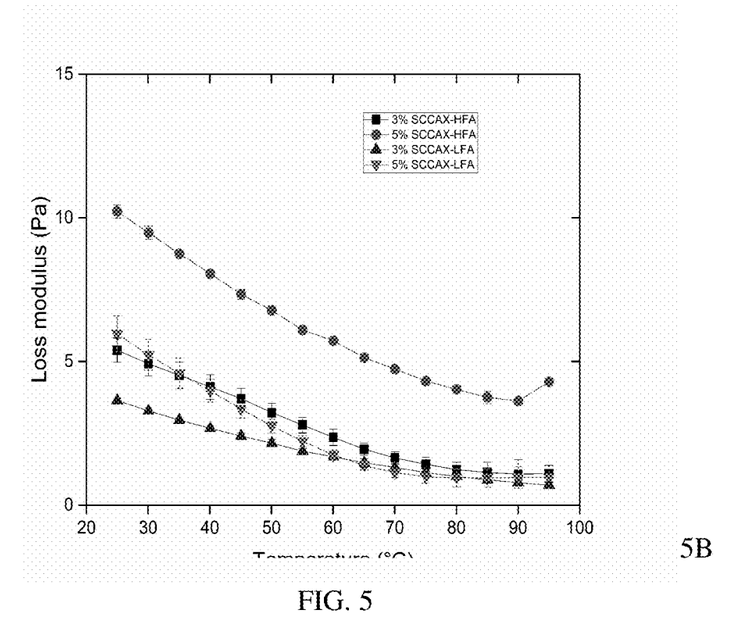
FIG. 5: The A) storage (G') and B) loss (G") moduli as a function of temperature for crosslinked arabinoxylan at pH 2 at a concentration of 3 wt % and 5 wt %. CAX-LFA and CAX-HFA are corn bran arabinoxylans extracted in 1.5 M and 0.25 M NaOH, respectively.
Figure 5A:
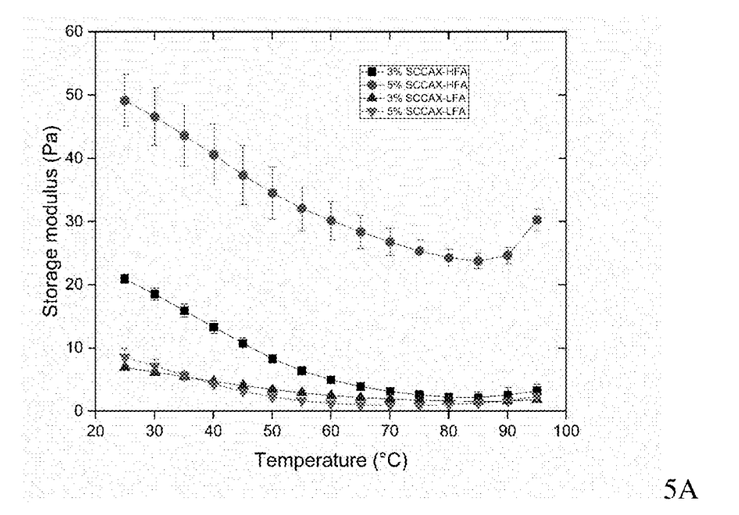

Effect of temperature on storage and loss moduli of arabinoxylans. To understand whether covalent bonds were involved in SCCAX gel formation at low pH, temperature sweeps of 3% and 5% of SCCAX-HFA and SCCAX-LFA at pH 2 were conducted. As shown in FIGS. 5A and 5B, SCCAX samples showed a clear decrease in storage and loss moduli, indicating that the forming of gels was not caused by covalent bonds, but the contribution of thermally reversible interactions. In addition, 5% SCCAX gels showed higher storage and loss moduli than 3% SCCAX gels, showing that higher concentration of SCCAX forms stronger gels. It was noteworthy that 3% SCCAX-HFA gels had higher storage and loss moduli than 5% SCCAX-LFA gels, showing that SCCAX-HFA forms much stronger gels than SCCAX-LFA.

Figure 6:
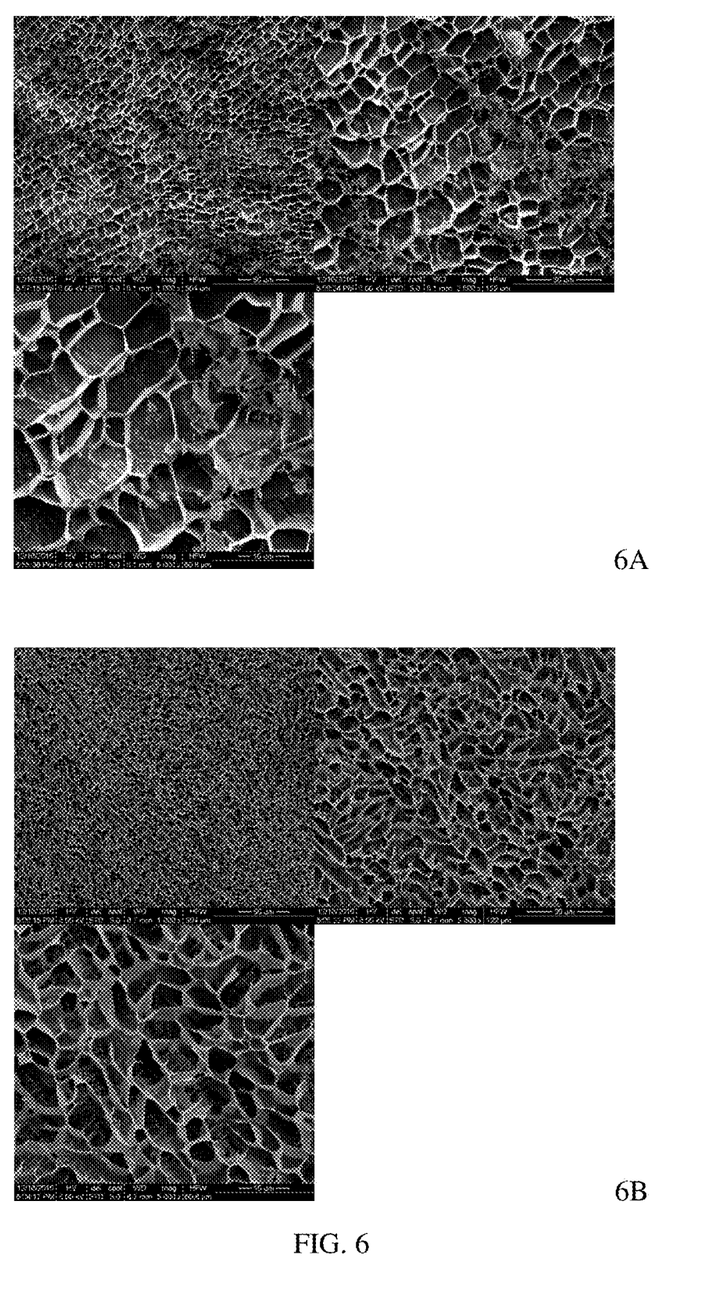
FIG. 6: Scanning electron micrograph image of A) SCCAX-LFA at pH 2; B) SCCAX-HFA at pH2. SCCAX-LFA is crosslinked corn bran arabinoxylan extracted in 1.5 M NaOH; SCCAX-HFA is crosslinked corn bran arabinoxylan extracted in 0.25 M NaOH.

Cryogenic scanning electron microscopy (Cryo-SEM) of arabinoxylan gels. Cryo-SEM images of 3% SCCAX-HFA and SCCAX-LFA gels made at different magnification levels are shown in FIG. 6. The structure of the gels was honeycomb-like. The diameter of the pores in SCCAX-LFA gel was around 10-20 μm, and SCCAX-HFA pores were less than 10 μm. The pore size of the SCCAX-HFA gel were clearly smaller than the SCCAX-LFA gel, which was in accordance with the rheological results. Overall, the SCCAX-HFA gel showed a more dense structure and was a stronger gel compared to the SCCAX-LFA gel.

Proposed mechanism of SCCAX gel forming at low pH. This disclosure may be the first report of arabinoxylan in aqueous solution forming a strong gel simply by lowering of pH to 2. Apparently, the critical step is the formation of soluble laccase-mediated polymeric complexes of diferulate-crosslinked arabinoxylan, which is the entity that participates in the gel formation at low pH. The data shows that noncovalent crosslinking was involved in the gel formation, because the gels were both pH and thermally reversible. Gellan gum also has similar acid gelling property to SCCAX, though the polymers are quite different in structure with gellan gum having linear mainchain repeating units with acyl substituents and arabinoxylan being branched polysaccharide. Thus, the mechanisms of gel formation may be different.

The proposed mechanism of formation of SCCAX to a gel is as follows. When pH decreases to 2, which is lower than the pKa of the glucuronic acid (pKa 3.21), the carboxylate groups (see Table 1) are protonated and became uncharged. As the result, the repulsive force between the polymer chains within the SCCAX complex decreases, giving polymer chains more of the characteristic of long neutral molecules. This, combined with the diferulate crosslinks found within the SCCAX complex, draws the polymers within the complex in close proximity with each other, allowing for hydrogen bonding between chains to develop. It is showed that 5'5-DFA was decreased and 8,5(decarboxylated)-DFA was increased, which may favor the gel formation as the intra-chain bonds might be favored by 5'5-DFA which lead to reduction of elastic effectivity of arabinoxylan network. Moreover, higher protein content in SCCAX-LFA may have contributed to its lower gel strength (Table 1), perhaps due to hindrance by residual protein molecules to the non-covalent interactions that likely occur among CAX chains during gelation. In addition, the low arabinose to xylose ratio of the SCCAX could favor the aggregation of arabinoxylan chains, and enhanced hydrogen bonding to drive a physical interaction between arabinoxylan chains. In turn, the neutral SCCAX complexes in solution aggregate to form gels at pH 2, which may be explained by a combination of hydrophobic interaction and hydrogen bond forces.

Surface charges of arabinoxylan. The surface charges of CAX-LFA, CAX-HFA, SCCAX-LFA, and SCCAX-HFA solutions were measured using a zeta-potential analyzer. As shown in Table 4, all the arabinoxylan samples were negatively charged, which was caused by the dissociation of carboxyl groups of branched uronic acid. The ζ-potentials of CAX-LFA, SCCAX-LFA, CAX-HFA, and SCCAX-HFA were −11.1, −13.4, −11.6, and −15.2 mV, respectively. No significantly different surface charge density was found between CAX-LFA and CAX-HFA. After crosslinking, the surface negative charge was significantly increased, indicating the success in crosslinking of arabinoxylan under laccase treatment. Moreover, SCCAX-HFA showed highest negative charge, confirming that higher crosslinking density was formed in SCCAX-HFA. Taken together, dense soluble structures formed with laccase (denser in the SCCAX-HFA) and, when protonated (ferulic and glucuronic acid residues) at low pH, the resulting uncharged, neutral polymeric structures presumably formed gel aggregates through hydrophobic and hydrogen bond interactions.

TABLE 4

| | Zeta-potential of arabinoxylan samples[d] | | | |
|---|---|---|---|---|
| Samples | CAX-LFA | SCCAX-LFA | CAX-HFA | SCCAX-HFA |
| zeta potential (mV) | −11.1c ± 0.8 | −13.4b ± 0.4 | −11.6c ± 0.9 | −15.2a ± 0.1 |

[d]CAX-LFA and CAX-HFA stand for corn bran arabinoxylan extracted by 1.5M and 0.25M NaOH, respectively; SCCAX-LFA and SCCAX-HFA stand for crosslinked CAX-LFA and CAX-HFA, respectively. Data are expressed as mean ± SD (n = 3). Sample values marked by the different letters are significant different (P < 0.05).

Figure 7:
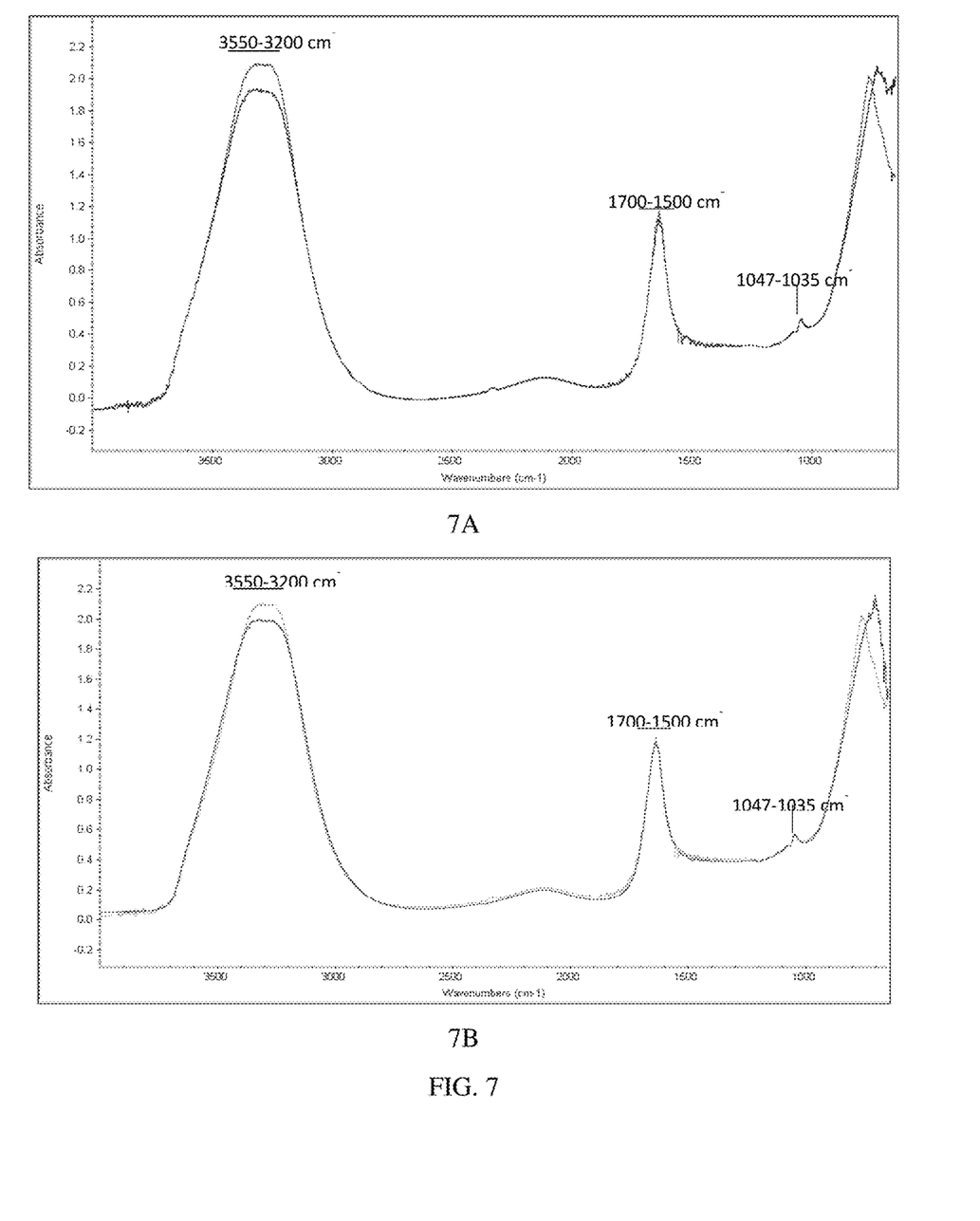
FIG. 7: FT-IR spectra of A) SCCAX-HFA at pH 2 and 5. The red line represents SCCAX-HFA at pH 5 and the blue line represents SCCAX-HFA at pH 2; B) SCCAX-LFA at pH 2 and 5. The green line represents SCCAX-LFA at pH 2 and the red line represents SCCAX-LFA at pH 5.

FT-IR spectra of SCCAX complex at different pH. To further understand the gel forming mechanism of SCCAX complexes, FT-IR was used to determine their structure at different pH's. FIG. 7 shows the FT-IR spectrum of SCCAX-HFA and SCCAX-LFA at pH 2 and pH 5 in the 500-4000 $cm^{-1}$ region. The characteristic absorption bands at 3200-3550 $cm^{-1}$ (broad) represents the hydroxyl-stretching vibrations of polysaccharides and water involved in hydrogen bonds. As shown in FIG. 7, the absorption intensity of SCCAX-HFA and SCCAX-LFA at pH 2 was significantly higher than that at pH 5, suggesting that the decrease of pH increased intermolecular hydrogen bond interaction. The results indicate that intermolecular hydrogen bonds play an important role in the gel forming of SCCAX at low pH. In addition, the characteristic absorption region between 800-1500$^{-1}$ cm represents C—C, C—O, C—OH and C—O—C stretch of arabinoxylan backbone, and 1500-1700$^{-1}$ cm region represents the absorption bands of ferulic acid and protein. Notably, the absorbance band at 1035-1047 $cm^{-1}$ represents the β (1-4) linked xylose backbone, whereas the peak intensity in our samples was relatively low. This might due to the low concentration of SCCAX (3%) used for the FT-IR analysis. Taken together, the surface charges of arabinoxylan samples, structural features including ferulic acid contents, molecular size and FT-IR data of arabinoxylans supported our proposed gel forming mechanism of SCCAX at low pH.

In summary, this disclosure describes a new polysaccharide-based gel, where a stable solution of 3.5 to 4.5-mer arabinoxylan complexes readily forms a gel simply by lowering pH. It was previously reported that arabinoxylan extracted with low alkali concentration (0.25 or 0.5 M NaOH) formed gels at pH 5 when treated with laccase. However, in the current study, no gel was formed at pH 5 for either SCCAX-LFA and SCCAX-HFA. It is believed that this was caused by the unusually low arabinose/xylose ratio of the CAX used (~0.22), and the coinciding low ferulic acid content of arabinoxylan in our study. Results support a view that the laccase-crosslinked SCCAX formed low pH gels due to hydrogen bond and hydrophobic interactions. Some applications may be obtained from SCCAX-formed gels, such as low sugar, low pH gels and a beverage, when consumed, that may gel in the low pH environment of the stomach to delay gastric emptying and increase satiety, as well as for other food gels and nutraceutical or drug delivery.

Those skilled in the art will recognize that numerous modifications can be made to the specific implementations described above. The implementations should not be limited to the particular limitations described. Other implementations may be possible.

We claim:

1. A hydrogel, wherein the hydrogel has a pH value of 1.5-2.5, wherein the hydrogel is a reaction product of a water-soluble laccase cross-linked arabinoxylan and an acid.

2. The hydrogel of claim 1, wherein the acid is a water-soluble inorganic acid.

3. The hydrogel of claim 1, wherein the acid is hydrochloric acid.

4. The hydrogel of claim 1, wherein the hydrogel has a pH value of 1.8-2.2.

5. The hydrogel of claim 1, wherein noncovalent cross-linking is involved in the gel formation during the reaction between the water-soluble laccase cross-linked arabinoxylan and an acid.

6. The hydrogel of claim 1, wherein the hydrogel is a pH-reversible gel.

7. The hydrogel of claim 1, wherein the hydrogel is a thermally reversible gel.

8. The hydrogel of claim 1, wherein the arabinoxylan used for laccase crosslinking is obtained from an alkali-treated corn bran.

9. The hydrogel of claim 8, wherein the alkali is KOH or NaOH.

10. The hydrogel of claim 1, wherein the arabinoxylan used for laccase crosslinking had an arabinose/xylose ratio between 0.15 to 0.3.

11. The hydrogel of claim 1, wherein the laccase cross-linked arabinoxylan has a 2-10 wt %.

12. A food or beverage product to which the hydrogel of claim 1 has been added as a low-sugar and low-pH additive.

* * * * *